(12) United States Patent
Ortiz et al.

(10) Patent No.: US 7,892,250 B2
(45) Date of Patent: Feb. 22, 2011

(54) USE OF BIOSURGICAL ADHESIVE ON INFLATABLE DEVICE FOR GASTRIC RESTRICTION

(75) Inventors: Mark S. Ortiz, Milford, OH (US); Randal T. Byrum, Kings Mills, OH (US); Fredrick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 742 days.

(21) Appl. No.: 11/555,322

(22) Filed: Nov. 1, 2006

(65) Prior Publication Data

US 2008/0103593 A1     May 1, 2008

(51) Int. Cl.
*A61M 29/00* (2006.01)
(52) U.S. Cl. ...................................... 606/195
(58) Field of Classification Search ......... 606/191–199, 606/213, 153, 108, 202; 623/23.65–23.67; 604/96.01, 516, 104–109; 128/898
See application file for complete search history.

(56) References Cited

U.S. PATENT DOCUMENTS

| | | | | |
|---|---|---|---|---|
| 4,311,146 | A | * | 1/1982 | Wonder ...................... 606/195 |
| 4,315,509 | A | * | 2/1982 | Smit ........................... 606/108 |
| 4,416,267 | A | * | 11/1983 | Garren et al. ................ 128/898 |
| 4,723,547 | A | * | 2/1988 | Kullas et al. ................. 606/185 |
| 4,735,214 | A | * | 4/1988 | Berman ....................... 600/572 |
| 4,735,616 | A | | 4/1988 | Eibl et al. |
| 4,766,898 | A | | 8/1988 | Hardy et al. |
| 4,874,368 | A | | 10/1989 | Miller et al. |
| 4,899,747 | A | * | 2/1990 | Garren et al. ................ 606/192 |
| 5,004,469 | A | | 4/1991 | Palmieri et al. |

(Continued)

FOREIGN PATENT DOCUMENTS

EP        0315222 B1     11/1992

(Continued)

OTHER PUBLICATIONS

Ikeda, et al.; "Auxiliary Tool for Device for Applying Adhesive on Living Tissue;" published in Japan [translated abstract for Patent Application No. JP2000286958]; Jun. 12, 2001.

(Continued)

*Primary Examiner*—Julian W Woo
*Assistant Examiner*—Christopher L Templeton
(74) *Attorney, Agent, or Firm*—Frost Brown Todd LLC (57) ABSTRACT

An apparatus for forming a gastric restriction comprises an applier, an expandable member, and an adhesive. The applier comprises an elongate shaft, and is dimensioned to fit in an esophagus. The applier has a conduit configured to communicate a fluid medium. The expandable member is in fluid communication with the conduit of the applier. The adhesive is positioned on at least a portion of the outer surface of the expandable member. The adhesive is configured to adhere the expanded expandable member to the inner wall of a patient's stomach. The expandable member may have a generally toroid configuration with a stoma, such that the expandable member may provide a gastric restriction when expanded and adhered to the inner wall of a patient's stomach. The expandable member may thus provide a treatment for morbid obesity by reducing food intake, by reducing stomach volume, or otherwise.

4 Claims, 6 Drawing Sheets

U.S. PATENT DOCUMENTS

| | | | |
|---|---|---|---|
| 5,108,370 A * | 4/1992 | Walinsky | 604/102.02 |
| 5,154,320 A | 10/1992 | Bolduc | |
| 5,181,921 A * | 1/1993 | Makita et al. | 606/195 |
| 5,234,454 A * | 8/1993 | Bangs | 606/191 |
| 5,254,113 A | 10/1993 | Wilk | |
| 5,312,333 A | 5/1994 | Churinetz et al. | |
| 5,324,305 A | 6/1994 | Kanner | |
| 5,372,585 A | 12/1994 | Tiefenbrun et al. | |
| 5,443,481 A | 8/1995 | Lee | |
| 5,474,540 A | 12/1995 | Miller et al. | |
| 5,529,577 A | 6/1996 | Hammerslag | |
| 5,582,596 A | 12/1996 | Fukunaga et al. | |
| 5,605,541 A | 2/1997 | Holm | |
| 5,718,711 A | 2/1998 | Berenstein et al. | |
| 5,752,965 A | 5/1998 | Francis et al. | |
| 5,759,169 A | 6/1998 | Marx | |
| 5,759,171 A | 6/1998 | Coelho et al. | |
| 5,765,559 A * | 6/1998 | Kim | 128/207.15 |
| 5,779,672 A * | 7/1998 | Dormandy, Jr. | 604/99.04 |
| 5,814,022 A | 9/1998 | Antanavich et al. | |
| 5,844,087 A | 12/1998 | Zimmerman et al. | |
| 5,895,412 A | 4/1999 | Tucker | |
| 5,904,701 A * | 5/1999 | Daneshvar | 606/192 |
| 5,928,611 A | 7/1999 | Leung | |
| 5,981,621 A | 11/1999 | Clark et al. | |
| 5,997,546 A * | 12/1999 | Foster et al. | 606/108 |
| 6,007,515 A | 12/1999 | Epstein et al. | |
| 6,010,714 A | 1/2000 | Leung et al. | |
| 6,055,828 A | 5/2000 | Rivera et al. | |
| 6,071,263 A * | 6/2000 | Kirkman | 604/104 |
| 6,099,807 A | 8/2000 | Leung | |
| 6,113,571 A | 9/2000 | Zinger et al. | |
| 6,143,352 A | 11/2000 | Clark et al. | |
| 6,143,805 A | 11/2000 | Hickey et al. | |
| 6,162,239 A | 12/2000 | Manhes | |
| 6,174,919 B1 | 1/2001 | Hickey | |
| 6,183,593 B1 | 2/2001 | Narang et al. | |
| 6,206,905 B1 | 3/2001 | Holm et al. | |
| 6,217,603 B1 | 4/2001 | Clark et al. | |
| 6,228,051 B1 | 5/2001 | Trumbull | |
| 6,234,994 B1 | 5/2001 | Zinger | |
| 6,245,933 B1 | 6/2001 | Malofsky et al. | |
| 6,280,399 B1 | 8/2001 | Rossin et al. | |
| 6,283,933 B1 | 9/2001 | D'Alessio et al. | |
| 6,302,898 B1 | 10/2001 | Edwards et al. | |
| 6,306,243 B1 | 10/2001 | Clark et al. | |
| 6,310,166 B1 | 10/2001 | Hickey et al. | |
| 6,322,852 B1 | 11/2001 | Leung | |
| 6,325,810 B1 | 12/2001 | Hamilton et al. | |
| 6,340,097 B1 | 1/2002 | D'Alessio et al. | |
| 6,352,704 B1 | 3/2002 | Nicholson et al. | |
| 6,372,313 B1 | 4/2002 | D'Alessio et al. | |
| 6,376,019 B1 | 4/2002 | Leung | |
| 6,394,975 B1 | 5/2002 | Epstein | |
| 6,394,982 B1 | 5/2002 | Ehrenfels | |
| 6,398,797 B2 | 6/2002 | Bombard et al. | |
| 6,412,639 B1 | 7/2002 | Hickey | |
| 6,420,590 B1 | 7/2002 | Badejo et al. | |
| 6,425,704 B2 | 7/2002 | Voiers et al. | |
| 6,428,233 B1 | 8/2002 | Clark et al. | |
| 6,428,234 B1 | 8/2002 | Bobo et al. | |
| 6,432,084 B1 | 8/2002 | Levinson et al. | |
| 6,433,096 B1 | 8/2002 | Hickey et al. | |
| 6,439,789 B1 | 8/2002 | Balance et al. | |
| 6,454,739 B1 | 9/2002 | Chang | |
| 6,454,785 B2 * | 9/2002 | De Hoyos Garza | 606/192 |
| 6,455,064 B1 | 9/2002 | Narang et al. | |
| 6,458,095 B1 | 10/2002 | Wirt et al. | |
| 6,461,361 B1 | 10/2002 | Epstein | |
| 6,461,367 B1 | 10/2002 | Kirsch et al. | |
| 6,464,663 B1 | 10/2002 | Zinger | |
| 6,468,520 B1 | 10/2002 | Rowe et al. | |
| 6,471,670 B1 | 10/2002 | Enrenfels et al. | |
| 6,478,191 B1 | 11/2002 | D'Alessio et al. | |
| 6,488,197 B1 | 12/2002 | Whitman | |
| 6,488,650 B1 | 12/2002 | Epstein et al. | |
| 6,488,944 B2 | 12/2002 | Narang | |
| 6,491,201 B1 | 12/2002 | Whitman | |
| 6,494,896 B1 | 12/2002 | D'Alessio et al. | |
| 6,512,023 B1 | 1/2003 | Malofsky et al. | |
| 6,527,749 B1 | 3/2003 | Roby et al. | |
| 6,540,716 B1 | 4/2003 | Holm | |
| 6,547,467 B2 | 4/2003 | Quintero | |
| 6,565,840 B1 | 5/2003 | Clark et al. | |
| 6,579,469 B1 | 6/2003 | Nicholson et al. | |
| 6,585,967 B2 | 7/2003 | Narang et al. | |
| 6,589,269 B2 | 7/2003 | Zhu et al. | |
| 6,592,281 B2 | 7/2003 | Clark et al. | |
| 6,595,940 B1 | 7/2003 | D'Alessio et al. | |
| 6,599,304 B1 * | 7/2003 | Selmon et al. | 606/159 |
| 6,602,496 B2 | 8/2003 | Hedgpeth et al. | |
| 6,605,667 B1 | 8/2003 | Badejo et al. | |
| 6,607,631 B1 | 8/2003 | Badejo et al. | |
| 6,613,020 B1 | 9/2003 | Holm et al. | |
| 6,616,019 B2 | 9/2003 | D'Alessio et al. | |
| 6,620,846 B1 | 9/2003 | Jonn et al. | |
| 6,637,967 B2 | 10/2003 | Bobo et al. | |
| 6,666,873 B1 | 12/2003 | Cassell | |
| 6,676,322 B1 | 1/2004 | Leung | |
| 6,681,979 B2 | 1/2004 | Whitman | |
| 6,695,199 B2 | 2/2004 | Whitman | |
| 6,705,790 B2 | 3/2004 | Quintero et al. | |
| 6,743,858 B2 | 6/2004 | Hickey et al. | |
| 6,746,460 B2 * | 6/2004 | Gannoe et al. | 606/153 |
| 6,746,667 B2 | 6/2004 | Badejo et al. | |
| 6,748,950 B2 | 6/2004 | Clark et al. | |
| 6,755,869 B2 * | 6/2004 | Geitz | 623/23.65 |
| 6,764,467 B1 | 7/2004 | Roby et al. | |
| 6,767,552 B2 | 7/2004 | Narang | |
| 6,779,657 B2 | 8/2004 | Mainwaring et al. | |
| 6,783,514 B2 | 8/2004 | Tovey et al. | |
| 6,802,416 B1 | 10/2004 | D'Alessio et al. | |
| 6,802,822 B1 | 10/2004 | Dodge | |
| 6,811,341 B2 | 11/2004 | Crane | |
| D500,085 S | 12/2004 | Cotter et al. | |
| 6,837,027 B2 | 1/2005 | Hickey | |
| 6,863,660 B2 | 3/2005 | Marx | |
| 6,884,232 B1 | 4/2005 | Hagmann et al. | |
| 6,896,684 B2 | 5/2005 | Monassevitch et al. | |
| 6,896,838 B2 | 5/2005 | D'Alessio | |
| 6,921,381 B2 | 7/2005 | Spero et al. | |
| 6,932,829 B2 * | 8/2005 | Majercak | 606/198 |
| 6,942,875 B2 | 9/2005 | Hedgpeth | |
| 6,960,040 B2 | 11/2005 | D'Alessio et al. | |
| 6,994,715 B2 * | 2/2006 | Gannoe et al. | 606/153 |
| 7,025,753 B2 * | 4/2006 | Reever | 604/327 |
| 7,025,776 B1 * | 4/2006 | Houser et al. | 606/213 |
| 7,033,373 B2 * | 4/2006 | de la Torre et al. | 606/191 |
| 7,037,344 B2 | 5/2006 | Kagan et al. | |
| 7,470,251 B2 * | 12/2008 | Shah | 604/96.01 |
| 2002/0012678 A1 | 1/2002 | Narang | |
| 2002/0037310 A1 | 3/2002 | Jonn et al. | |
| 2002/0048480 A1 | 4/2002 | D'Alessio et al. | |
| 2002/0055573 A1 | 5/2002 | Malofsky et al. | |
| 2002/0065336 A1 | 5/2002 | Hickey et al. | |
| 2002/0119184 A1 | 8/2002 | Nicholson et al. | |
| 2002/0147462 A1 | 10/2002 | Mair et al. | |
| 2002/0156203 A1 | 10/2002 | Hickey et al. | |
| 2002/0157675 A1 | 10/2002 | Clark et al. | |
| 2002/0165483 A1 | 11/2002 | Miller et al. | |
| 2002/0173770 A1 | 11/2002 | Flory et al. | |
| 2002/0173771 A1 * | 11/2002 | Dono | 604/540 |
| 2002/0176732 A1 | 11/2002 | Quintero et al. | |
| 2002/0176733 A1 | 11/2002 | Clark et al. | |

| | | |
|---|---|---|
| 2002/0185396 A1 | 12/2002 | Mainwaring et al. |
| 2002/0192011 A1 | 12/2002 | Bobo et al. |
| 2002/0192107 A1 | 12/2002 | Hickey |
| 2003/0007826 A1 | 1/2003 | Badejo et al. |
| 2003/0007946 A1 | 1/2003 | Narang et al. |
| 2003/0007947 A1 | 1/2003 | Narang |
| 2003/0007948 A1 | 1/2003 | Hedgpeth |
| 2003/0007949 A1 | 1/2003 | Hedgpeth et al. |
| 2003/0015557 A1 | 1/2003 | D'Alessio et al. |
| 2003/0031499 A1 | 2/2003 | Heard et al. |
| 2003/0032833 A1 | 2/2003 | Badejo et al. |
| 2003/0039781 A1 | 2/2003 | D'Alessio et al. |
| 2003/0044219 A1 | 3/2003 | Quintero |
| 2003/0060380 A1 | 3/2003 | Ayarza et al. |
| 2003/0063944 A1 | 4/2003 | Leung |
| 2003/0080151 A1 | 5/2003 | D'Alessio et al. |
| 2003/0082116 A1 | 5/2003 | Badejo et al. |
| 2003/0096069 A1 | 5/2003 | D'Alessio |
| 2003/0149128 A1 | 8/2003 | Malofsky et al. |
| 2003/0181964 A1 | 9/2003 | Sharkey et al. |
| 2003/0202956 A1 | 10/2003 | Clark et al. |
| 2003/0220666 A1* | 11/2003 | Mirigian et al. ............. 606/200 |
| 2004/0026282 A1 | 2/2004 | D'Alessio et al. |
| 2004/0044354 A1* | 3/2004 | Gannoe et al. ............. 606/153 |
| 2004/0059283 A1 | 3/2004 | Kirwan et al. |
| 2004/0111115 A1 | 6/2004 | Maw |
| 2004/0120849 A1 | 6/2004 | Stewart et al. |
| 2004/0137067 A1 | 7/2004 | Narang et al. |
| 2004/0143290 A1 | 7/2004 | Brightbill |
| 2004/0151688 A1 | 8/2004 | Sherbondy et al. |
| 2004/0190975 A1 | 9/2004 | Goodman et al. |
| 2004/0223932 A1 | 11/2004 | Hedgpeth et al. |
| 2004/0223946 A1 | 11/2004 | Kidd et al. |
| 2004/0234578 A1 | 11/2004 | Chen et al. |
| 2004/0254561 A1 | 12/2004 | Stenton |
| 2005/0033328 A1 | 2/2005 | Laufer et al. |
| 2005/0042266 A1 | 2/2005 | Narang |
| 2005/0047846 A1 | 3/2005 | Narang et al. |
| 2005/0070935 A1 | 3/2005 | Ortiz |
| 2005/0145671 A1 | 7/2005 | Viola |
| 2005/0147457 A1 | 7/2005 | Badejo et al. |
| 2005/0175395 A1 | 8/2005 | Quintero et al. |
| 2005/0177226 A1* | 8/2005 | Banik et al. ................ 623/1.42 |
| 2005/0182443 A1 | 8/2005 | Jonn et al. |
| 2005/0184121 A1 | 8/2005 | Heinrich |
| 2005/0220849 A1 | 10/2005 | Hickey |
| 2005/0228446 A1 | 10/2005 | Mooradian et al. |
| 2005/0230453 A1 | 10/2005 | Viola |
| 2005/0256446 A1 | 11/2005 | Criscuolo et al. |
| 2005/0273060 A1* | 12/2005 | Levy et al. .................. 604/192 |
| 2006/0009099 A1 | 1/2006 | Jonn et al. |
| 2007/0038239 A1* | 2/2007 | Ritchie ...................... 606/192 |
| 2007/0118160 A1* | 5/2007 | Gannoe et al. ............. 606/153 |
| 2007/0198048 A1* | 8/2007 | Behan et al. ................ 606/194 |
| 2007/0250020 A1* | 10/2007 | Kim et al. .................. 604/264 |
| 2008/0097513 A1* | 4/2008 | Kaji et al. .................. 606/192 |
| 2009/0036910 A1* | 2/2009 | Kim et al. .................. 606/157 |

FOREIGN PATENT DOCUMENTS

| | | |
|---|---|---|
| EP | 0716833 A2 | 6/1996 |
| EP | 0648510 B1 | 11/1998 |
| EP | 0669100 B1 | 11/1998 |
| EP | 1078600 A2 | 2/2001 |
| EP | 1159081 A1 | 12/2001 |
| EP | 1381321 A2 | 1/2004 |
| EP | 1113839 B1 | 11/2004 |
| EP | 1073484 B1 | 8/2005 |
| EP | 1411836 B1 | 10/2005 |
| JP | 10262986 | 10/1998 |
| JP | 2000217830 | 8/2000 |
| JP | 2001157716 | 6/2001 |
| JP | 2001190558 | 7/2001 |
| JP | 2002233581 | 8/2002 |
| JP | 2003126268 | 5/2003 |
| JP | 2005028009 | 2/2005 |
| JP | 2005169125 | 6/2005 |
| WO | WO 92/09651 | 6/1992 |
| WO | WO 95/31137 A1 | 11/1995 |
| WO | WO 98/41154 A1 | 9/1998 |
| WO | WO 99/17833 A1 | 4/1999 |
| WO | WO 99/30629 A1 | 6/1999 |
| WO | WO 01/12257 A1 | 2/2001 |
| WO | WO 01/24869 A1 | 4/2001 |
| WO | WO 01/62158 A2 | 8/2001 |
| WO | WO 01/62162 A1 | 8/2001 |
| WO | WO 01/62333 A1 | 8/2001 |
| WO | WO 02/067785 A2 | 9/2002 |
| WO | WO 03/088845 | 10/2003 |

OTHER PUBLICATIONS

Ikeda, et al.; "Device for Applying Organism Tissue Adhesive;" published in Japan [translated abstract for Patent Application No. JP2000320375]; Jul. 17, 2001.

Gomibuchi, Makoto; "Medical Adhesive Applicator;" published in Japan [translated abstract for Patent Application No. JP11023146]; Aug. 8, 2000.

Ikeda, et al.; "Organism-Tissue Adhesive Applicator;" published in Japan [translated abstract for Patent Application No. JP2001033756]; Aug. 20, 2002.

Ikeda, et al.; "Biological Tissue Adhesive Applicator;" published in Japan [translated abstract for Patent Application No. JP2001323890]; May 7, 2003.

Arikawa, Seiki; "Biological Tissue Adhesive Applicator;" published in Japan [translated abstract for Patent Application No. JP2003273091]; Feb. 3, 2005.

Keller, Wilhelm A.; "Applicator for Dispensing Appliance;" published in Japan [translated abstract for Patent Application No. JP2004358509]; Jun. 30, 2005.

Sasaki, Hiroshi; "Adhesive Agent Applicator for Surgical Operation;" published in Japan [translated abstract for Patent Application No. JP09076817]; Oct. 6, 1998.

* cited by examiner

USE OF BIOSURGICAL ADHESIVE ON INFLATABLE DEVICE FOR GASTRIC RESTRICTION

BACKGROUND

Biosurgical adhesives have been used in a variety of ways in various medical procedures. An exemplary adhesive is disclosed in U.S. Pub. No. 2004/0190975, the disclosure of which is incorporated by reference herein. Similarly, a variety of devices and techniques have been used to deliver adhesives at various sites. In addition, gastric restrictions have been created using a variety of devices (e.g., gastric bands) and procedures, such as to treat morbid obesity. While several systems and methods have been made and used for using biosurgical adhesives, and several systems and methods have been used to create gastric restrictions, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

As shown in FIGS. 1-5, an exemplary applier device (10) is shown partially disposed within a patient's stomach (100). As shown, applier device (10) comprises a generally cylindraceous elongate shaft (12) having a rounded distal tip (14). In the present example, shaft (12) is generally flexible, and is dimensioned to be fed transorally through a patient's esophagus (not shown) to reach the stomach (100). Of course, shaft (12) may have any other suitable properties, dimensions, and/or features. A retractable sheath (16) is provided around shaft (12), and is operable to translate axially relative to shaft (12). In this example, sheath (16) is generally flexible in order to accommodate surface features or protrusions of shaft (12) as sheath (16) is moved relative to shaft (12). However, sheath (16) may have any other suitable properties, dimensions, and/or features. Furthermore, sheath (16) may be omitted altogether.

An inflatable member (20) is also provided about shaft (12). In the present example, inflatable member (20) comprises a silicone material, though any other suitable material(s) may be used. An adhesive material (22) is provided on the outer surface of inflatable member (20). By way of example only, adhesive material (22) may comprise a cyanoacrylate, an isocyanate, and/or any other suitable substance, including combinations of substances. For instance, and as will be described in greater detail below, adhesive material (22) may be configured to adhere to the inner wall (102) of a patient's stomach (100). In other words, and as will also be described in greater detail below, inflatable member (20) may be secured to the inner wall (102) of a patient's stomach (100) by adhesive material (22).

In the present example, sheath (16) and adhesive material (22) are configured such that, despite contact between sheath (16) and adhesive material (22), adhesive material (22) will not adhere to sheath (16). This may be accomplished in a variety of ways, including but not limited to a coating on the inner wall of sheath (16). Other techniques for preventing adhesive material (22) from adhering to sheath (16) will be apparent to those of ordinary skill in the art. In another variation, applier (10) is configured such that contact between sheath (16) and adhesive material (22) is avoided (e.g., by providing at least some degree of space between sheath (16) and adhesive material (22), by providing a buffer or guard of any suitable material between sheath (16) and adhesive material (22), etc.). In yet another variation, sheath (16) is substituted with a removable wrapping positioned about adhesive material (22). In still another variation, adhesive material (22) is not provided on inflatable member (20) when applier (10) is introduced to the stomach (100). In this variation, applier (10) comprises a feature (not shown) that is operable to dispense adhesive material (22) on inflatable member (22) after applier (10) has been introduced to the stomach (100) (e.g., and after sheath (16) has been retracted). Other suitable substitutes, supplements, and variations of sheath (16) and adhesive material (22) will be apparent to those of ordinary skill in the art.

Figure 1:
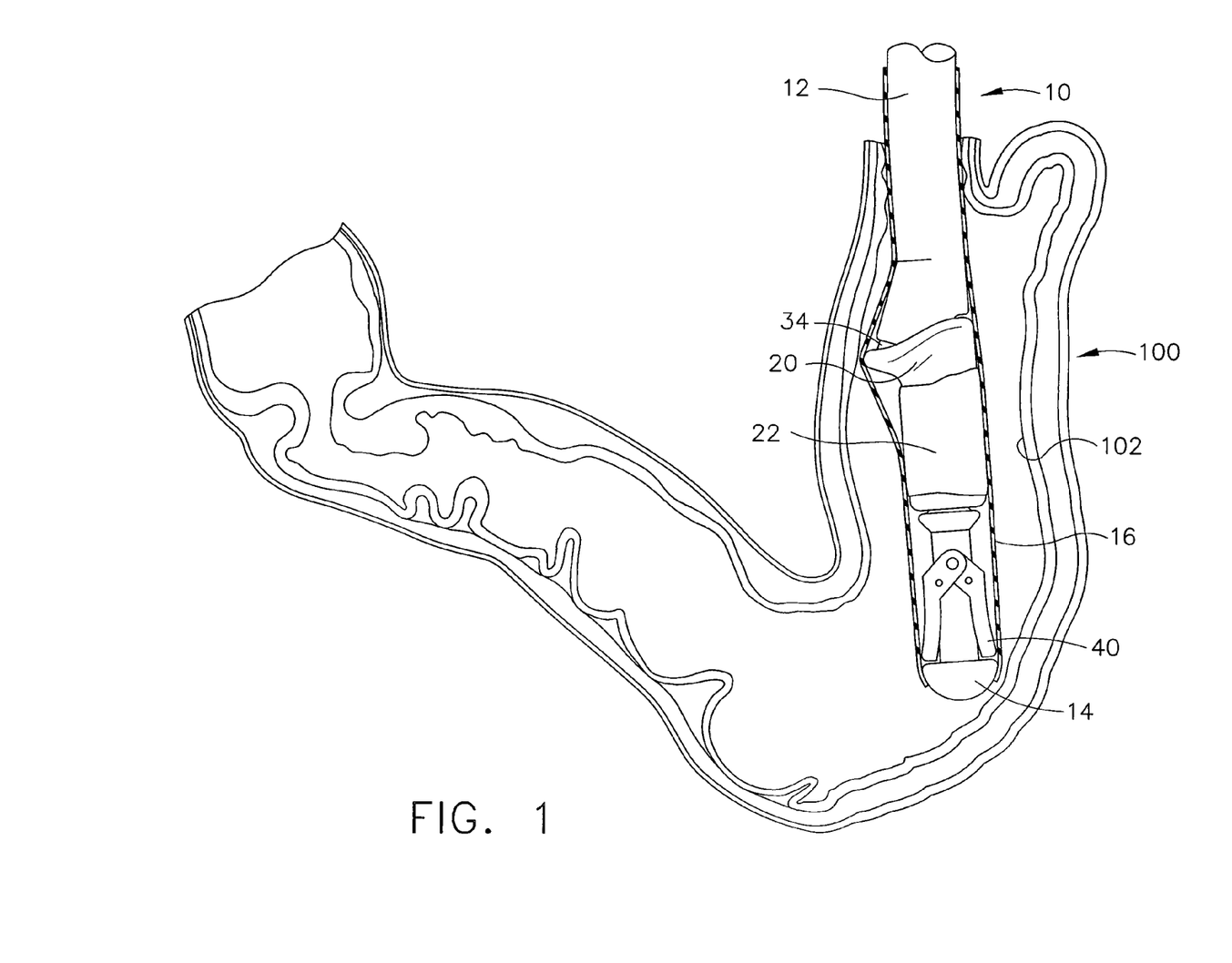
FIG. 1 depicts a partial side view of an exemplary applier device positioned within a stomach.
Figure 2:
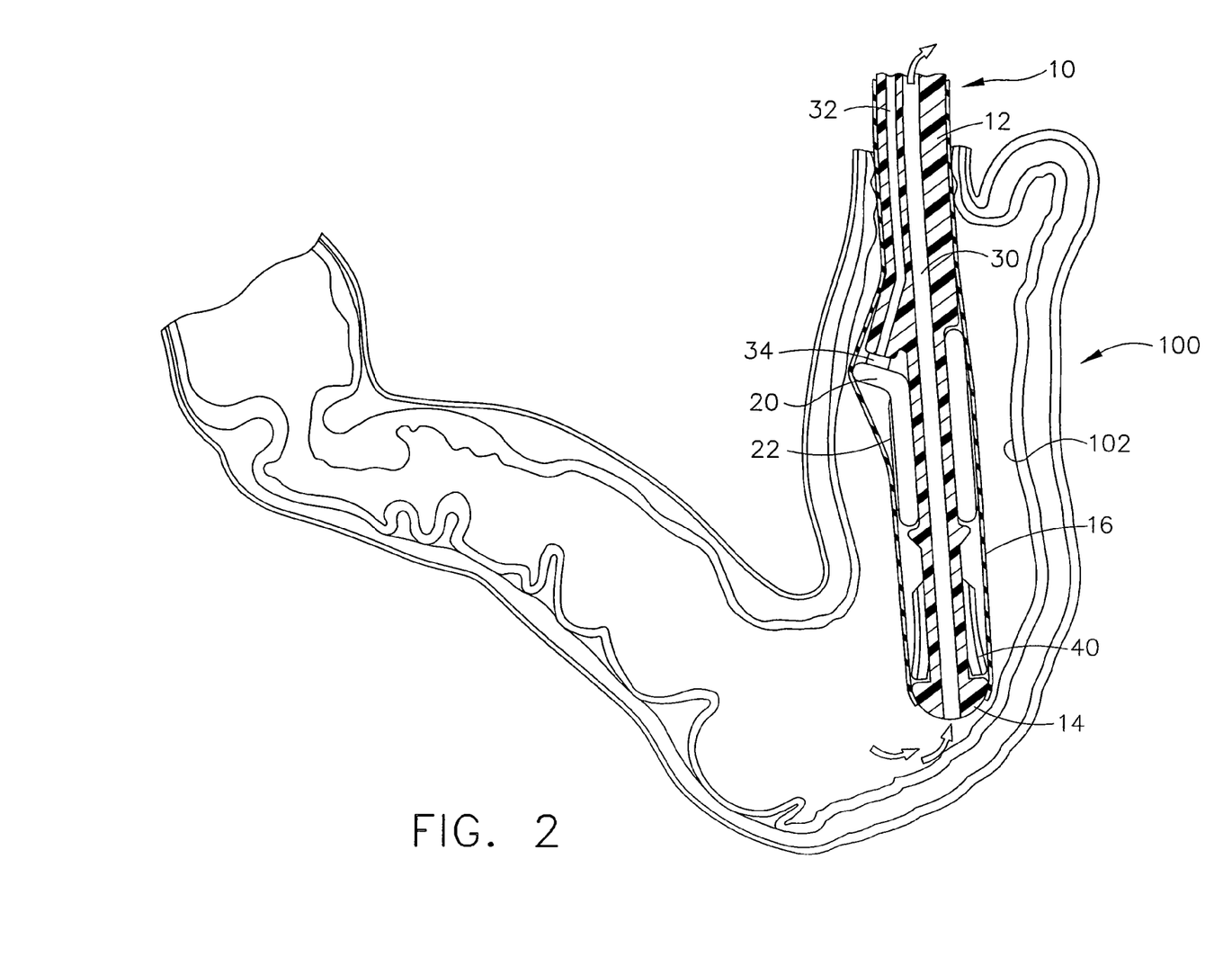
FIG. 2 depicts a cross-sectional view of the applier device of FIG. 1.
Figure 3:
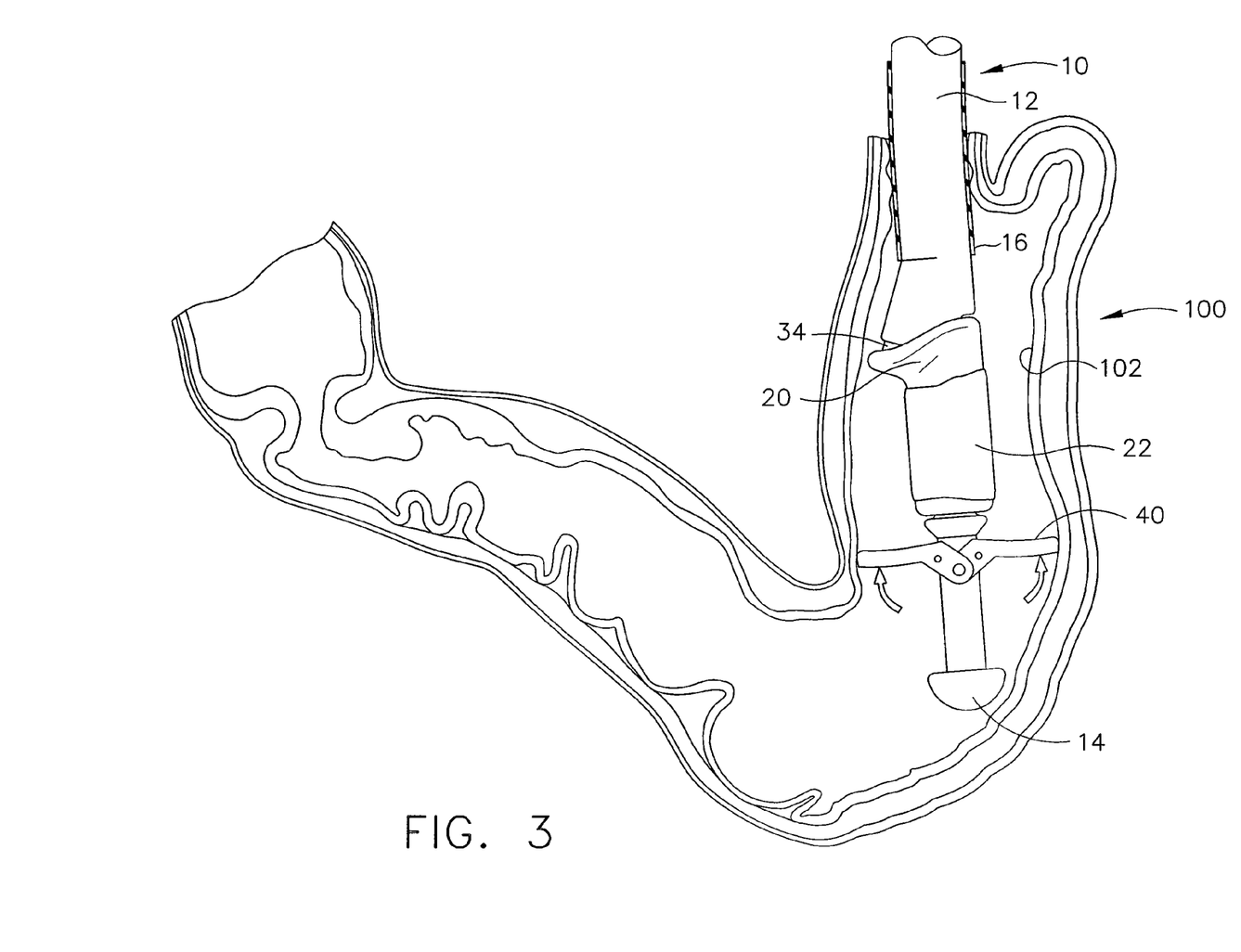
FIG. 3 depicts a partial view of the applier device of FIG. 1 with arms extended and with a retracted sheath.
Figure 4:
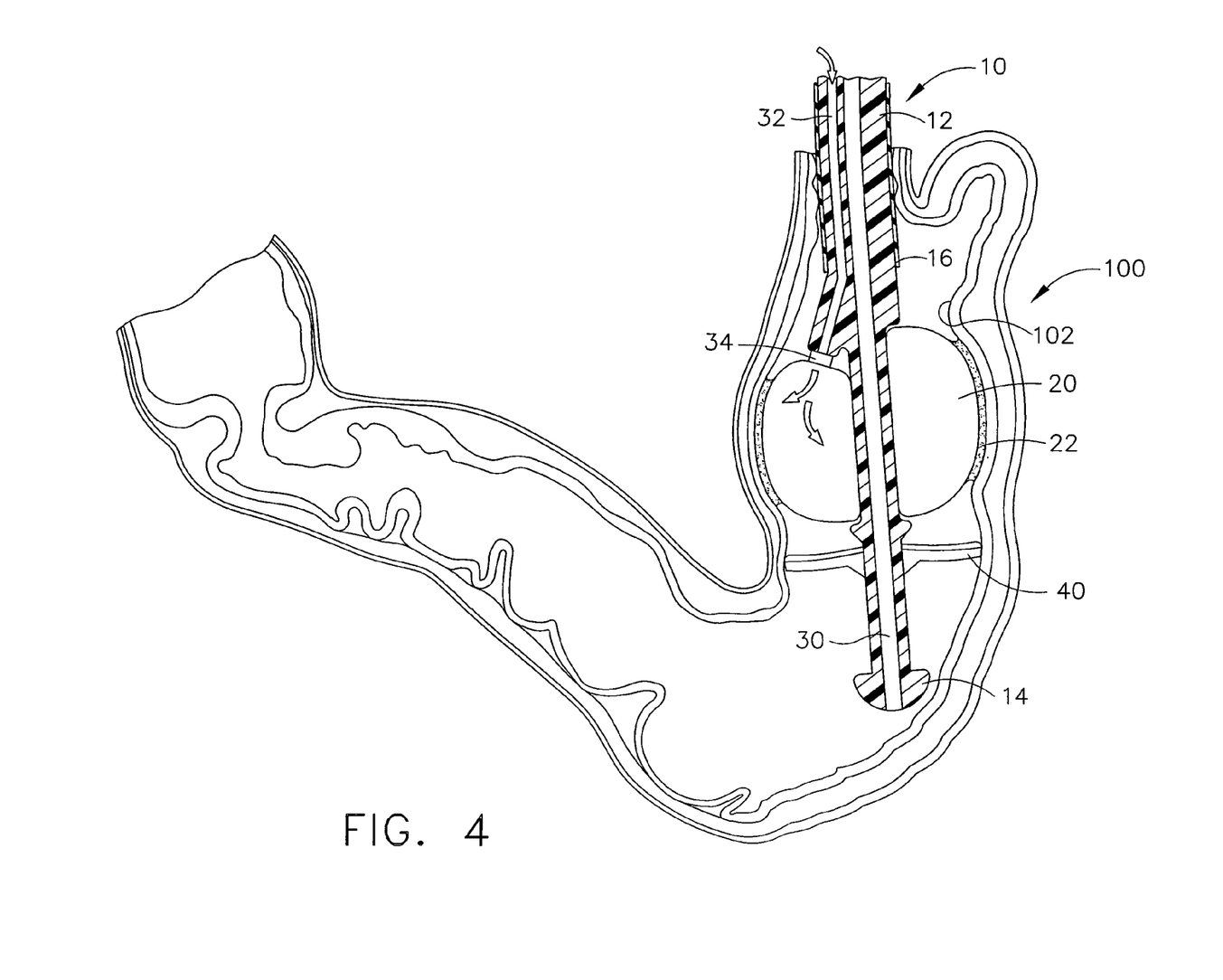
FIG. 4 depicts a partial cross-sectional view of the applier device of FIG. 1 with an exemplary inflatable member being inflated.

As shown in FIGS. 2 and 4, shaft (12) further comprises an axial lumen (30) and an inflation lumen (32). Axial lumen (30) extends longitudinally along the axis of shaft (12), and opens at distal tip (14) of shaft (12). Inflation lumen (32) extends longitudinally parallel to axial lumen (30), and opens at an inflation port (34). In the present example, when applier (10) is in the configurations shown in FIGS. 1-5, inflation port (34) is coupled with inflatable member (20), such that inflation port (34) and inflatable member (20) are in sealed fluid communication. For instance, inflation port (34) may be used to communicate a fluid such as a gas, liquid, and/or gel from inflation lumen (32) to inflatable member (20). Inflatable member (20) is further configured such that fluid communicated from inflation port (34) is retained within inflatable member (20), even after inflatable member (20) is separated from inflation port (34). For instance, inflatable member (20) may comprise a one-way valve or check valve (not shown) in communication with inflation port (34). Other suitable features for inflation port (34) and/or inflatable member (20) will be apparent to those of ordinary skill in the art. It will also be appreciated that inflatable member (20) may be substituted with a variety of alternative structures. For instance, a non-inflating expandable member may be used in lieu of or in addition to inflatable member (20), suitable examples of which will be apparent to those of ordinary skill in the art. In other words, one of ordinary skill in the art will appreciate that expansion of inflatable member (20), or of an alternative thereto, may be achieved by techniques and processes other than inflation. The inventors contemplate such alternative expansion as an option.

Figure 5:
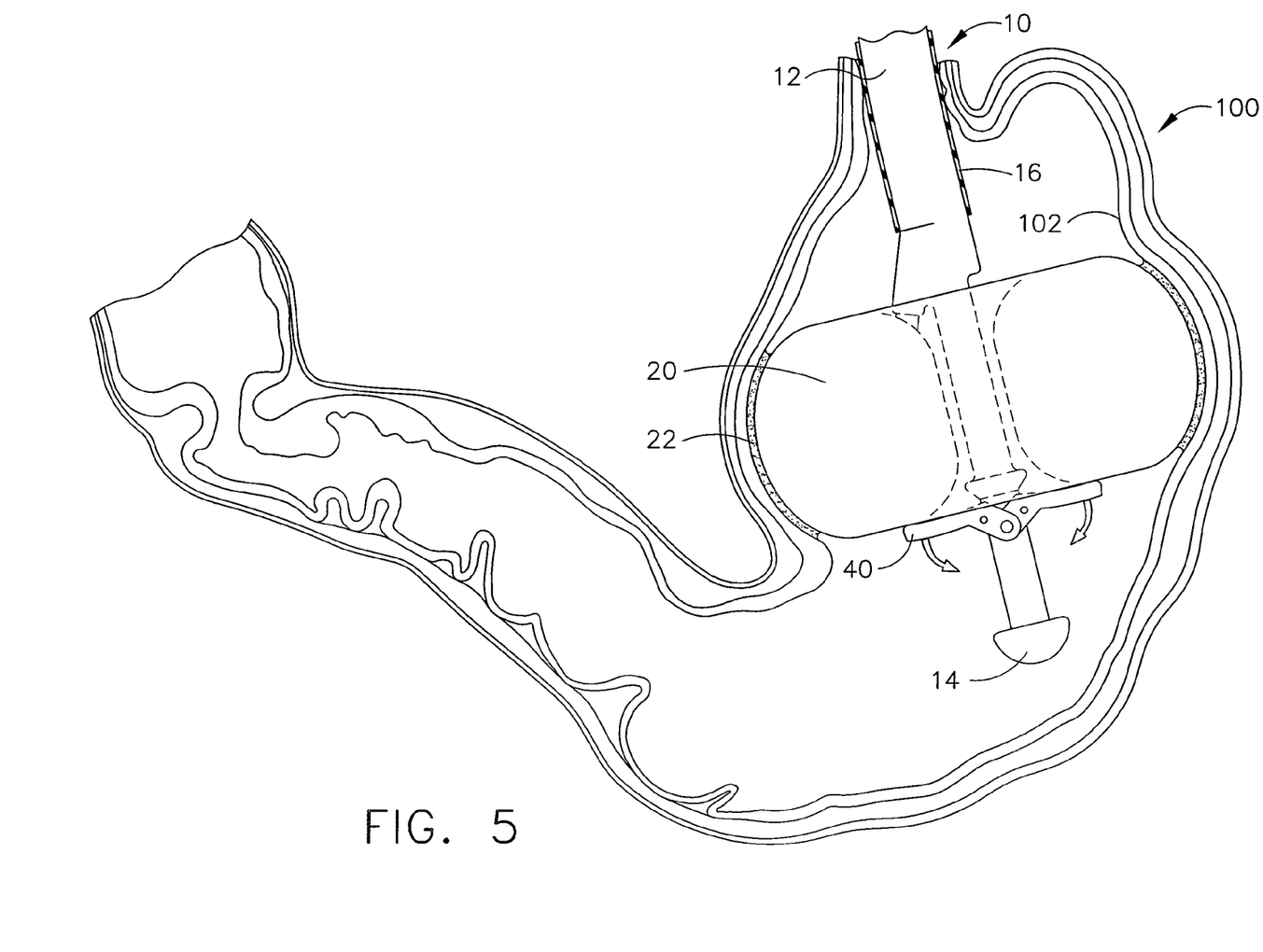
FIG. 5 depicts a partial view of the applier device of FIG. 1 with an inflatable member in an exemplary inflated state.

Applier (10) further comprises a pair of arms (40) located between inflatable member (20) and distal tip (14). Arms (40) are pivotally connected to shaft (12), and are operable to sweep outward. By way of example only, FIGS. 1-2 show arms (40) in a pre-deployed configuration, while FIGS. 3-5 show arms (40) in a deployed or swept configuration. In one embodiment, arms (40) are in communication with one or more cables (not shown) extending along or within shaft (12), such that arms (40) may be moved from a pre-deployed configuration to a deployed configuration by a user pulling or pushing on the one or more cables from a location proximal to arms (40). Of course, any other suitable mechanisms or techniques for moving arms (40) from a pre-deployed configuration to a deployed configuration may be used, including but not limited to threaded members, one or more motors, springs, electroactive polymers, rods, etc. In the present example, arms (40) are configured such that, when arms (40) are in a deployed configuration, arms (40) will provide support and/or restraint for inflatable member (20) as inflatable member (20) is inflated. However, arms (40) may also or alternatively serve a variety of other purposes.

While arms (40) are shown as moving from a pre-deployed configuration to a deployed configuration in a sweeping motion (e.g., rotating relative to shaft (12)), other suitable forms of movement may be used, including but not limited to movement in an only radially outward movement. Other suitable variations for arms (40) and movement of the same will be apparent to those of ordinary skill in the art. Alternatively, arms (40) may be supplemented or substituted by any other structure(s), or may be omitted altogether.

In an exemplary use of applier (10), applier (10) is inserted through the esophagus of a patient such that distal tip (14) enters the patient's stomach (100). During insertion of applier (10), sheath (16) is extended to cover shaft (12). An exemplary stage of insertion is illustrated in FIG. 1. Next, as shown in FIG. 2, a vacuum is induced within axial lumen (30) of applier (10). The vacuum may draw inner wall (102) of stomach (100) toward applier (10), and/or may provide other results. Of course, as with other acts described in this exemplary method of use, this act of inducing a vacuum may be modified or eliminated. For instance, axial lumen (30) may simply provide pressure relief to atmosphere. Alternatively, an imaging device may be inserted through axial lumen (30) to provide a view within stomach (100). As yet another non-exhaustive alternative, axial lumen (30) may be omitted altogether.

In the present example, with applier (10) longitudinally positioned, and with a vacuum having been induced (if employed), sheath (16) is longitudinally retracted to reveal arms (40), adhesive (22), and inflatable member (20) as shown in FIG. 3. As is also shown in FIG. 3, with sheath (16) retracted, arms (40) are swept outward to reach a deployed configuration. As is shown in FIG. 4, a pressurized fluid is communicated to inflatable member (20) via inflation lumen (32) and inflation port (34). By way of example only, such a pressurized fluid may comprise a gas such as air, etc., or a liquid such as saline, etc. Alternatively, a gel or other material may be communicated to inflatable member (20). In the present example, as inflatable member (20) expands, adhesive material (22) comes into contact with inner wall (102) of stomach (100). Adhesive material (22) is then able to secure inflatable member (20) relative to inner wall (102) of stomach (100).

As shown in FIG. 5, when inflatable member (20) has obtained a suitable level of inflation, expansion, or some other suitable type of state or configuration, arms (40) are swept back downward to the non-deployed configuration. In this example, an inflated inflatable member (20) has a generally toroid or donut-like configuration, though any other suitable configuration may be used. With arms (40) in a non-deployed configuration, and with inflated inflatable member (20) secured to inner wall (102) of stomach (100) via adhesive material (22), applier (10) is withdrawn through stoma (24) of inflated inflatable member (20) and through the esophagus of the patient. The inflated inflatable member (20) is left within the patient's stomach (100), secured to the inner wall (102) of stomach (100) via adhesive material (22) as shown in FIG. 6.

Suitable variations of the aforementioned method will be apparent to those of ordinary skill in the art. By way of example only, adhesive material (22) may be applied at an interface of inflatable member (20) and inner wall (102) of stomach (100) after inflatable member (20) has been positioned and inflated, in lieu of or in addition to adhesive material (22) being provided on inflatable member (20) prior to inflation. It will also be appreciated that the aforementioned method (and variations of the same) may be performed using devices other than applier (10) and/or inflatable member (20).

In one embodiment, the material of which inflatable member (20) is formed is configured such that inflatable member does not extend as fluid is introduced therein, or such that inflatable member extends only at a relatively minimal level. By way of example only, such a property of inflatable member may result in relatively low pressure inside inflatable member (20), such that the likelihood of fluid migrating through inflatable member may be reduced. Alternatively, inflatable member (20) may be extensible, resilient, or have any other suitable properties. In yet another variation, a size limiting loose weave mesh (not shown) or other device is provided about inflatable member (20) or within the wall of inflatable member (20), such that the size of inflated inflatable member (20) may be limited or capped (e.g., to not exceed a predetermined volume). Such a mesh or other device may further have an initiator material or other material incorporated thereon or therein to react with adhesive material (22).

Figure 6:
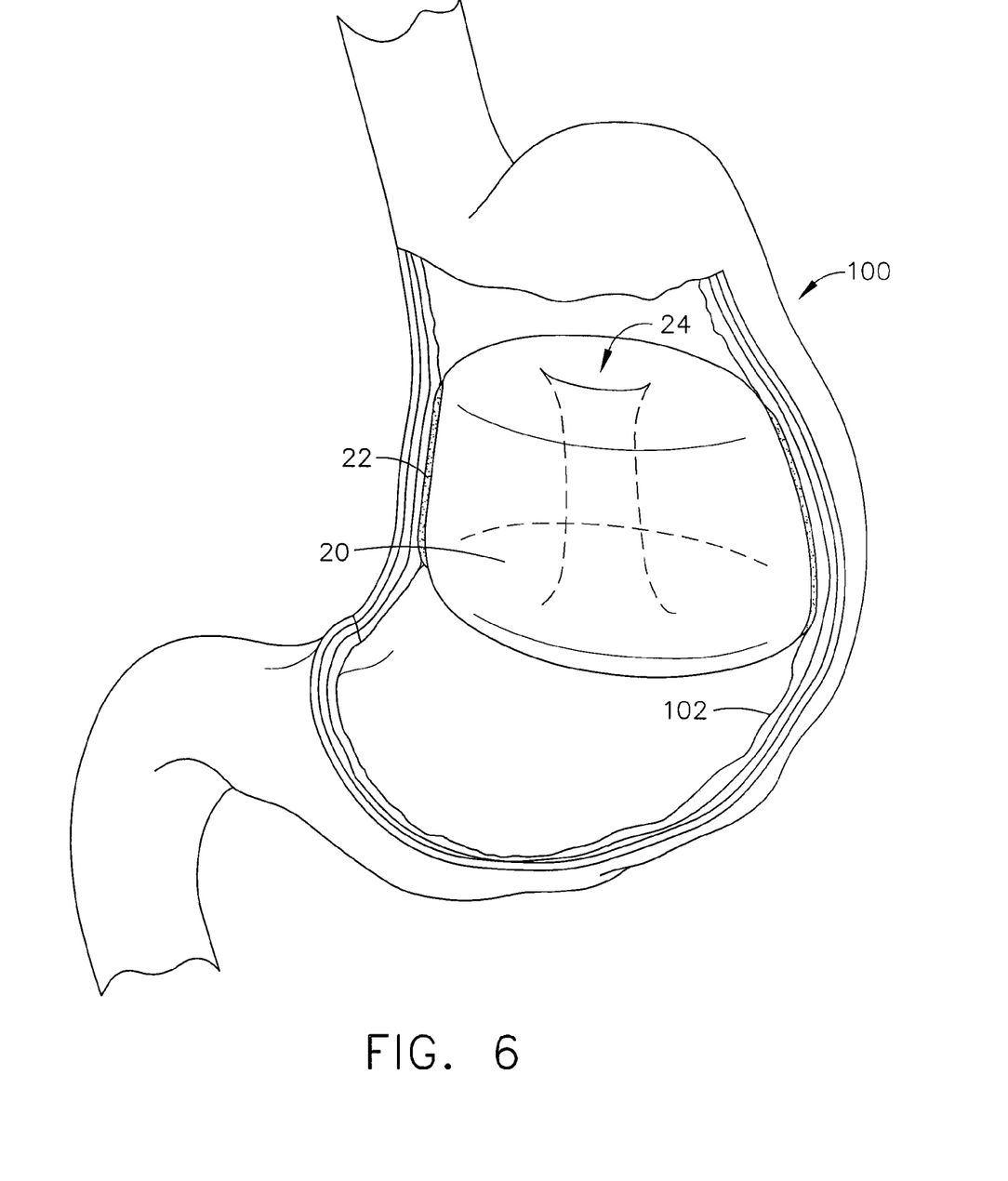
FIG. 6 depicts a side view of the inflatable member of FIG. 5 deployed within a stomach with the applier device of FIG. 1 withdrawn.

With inflated inflatable member (20) secured to the inner wall (102) of stomach (100) via adhesive material (22) as shown in FIG. 6, the stoma (24) within the donut-like configuration of inflatable member (20) may be sized to provide a gastric restriction similar to a restriction provided by a gastric band or other device. It will therefore be appreciated that inflatable member (20) may provide a treatment for morbid obesity by restricting food intake of patients. Furthermore, the size of the stoma (24) provided by inflatable member (20) may be fixed using a relatively stiff silicone cylinder (not shown) within stoma (24), or using another device or structure. Alternatively, inflatable member (20) may be configured such that the dimension of the stoma (24) may be varied as a function of the volume of fluid introduced into inflatable member (20). Other ways in which stoma (24) size may be fixed and/or adjusted will be apparent to those of ordinary skill in the art.

In addition to the flow restriction caused by the stoma (24) of inflatable member (20), inflatable member may provide reduction of the overall volume of stomach (100), which may further provide a treatment for morbid obesity by reducing the amount of food that may be contained within stomach (100) at a given time.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. the sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method of using an applier, an expandable member, and an adhesive to form a gastric flow restriction, wherein the applier comprises an elongate shaft and a distal tip, wherein the elongate shaft comprises a sheath retractable in a longitudinal direction relative to the shaft, wherein the sheath is configured such that the adhesive will not adhere to the sheath despite contact, wherein the applier is dimensioned to fit in an esophagus, wherein the applier has a conduit configured to communicate a fluid medium, wherein the expandable member is in fluid communication with the conduit of the applier, wherein the expandable member is configured to expand from a non-expanded configuration to an expanded configuration, wherein the expandable member has an outer surface, wherein a portion of the expandable member defines an opening that extends through the expandable member, wherein the shaft is positioned within the opening of the expandable member such that the shaft extends through the expandable member, wherein the applier further comprises one or more arms, wherein the one or more arms are configured to deploy about a respective pivot, the method comprising:

(a) inserting the applier and the expandable member through a patient's esophagus until the expandable member and at least a portion of the applier reach the patient's stomach, wherein the applier is positioned such that the applier extends through the opening of the expandable member with the distal tip positioned below the expandable member during the act of inserting;

(b) retracting the sheath in a longitudinal direction relative to the shaft while the shaft remains positioned within the opening of the expandable member;

(c) deploying the one or more arms, wherein the act of deploying the one or more arms comprises extending the one or more arms in an outward motion sweeping proximally towards the sheath such that extending the one or more arms results in forming a substantially horizontal platform, wherein the substantially horizontal platform is configured and positioned to support the expandable member;

(d) expanding the expandable member within the patient's stomach, wherein the act of expanding comprises communicating a fluid medium through the conduit while the shaft remains positioned within the opening of the expandable member, wherein the act of expanding comprises resting at least a portion of the expandable member on the substantially horizontal platform formed by the one or more arms, wherein the distal tip acts as a barrier to prevent the lower portion of the stomach from interfering with the expandable member during the act of expanding the expandable member;

(e) adhering a portion of the outer surface of the expanded expandable member to the inner wall of the patient's stomach with the adhesive to form a gastric flow restriction within the patient's stomach, wherein at least a portion of the gastric flow restriction is defined by the opening within the expandable member;

(f) retracting the one or more arms, wherein the act of retracting the one or more arms comprises inwardly sweeping the one or more arms such that the one or more arms sweep distally to position the one or more arms substantially parallel to the elongate shaft; and (g) removing the applier from the patient's stomach by removing the shaft from the opening of the expandable member.

2. The method of claim 1, further comprising providing the adhesive on the outer surface of the expandable member, wherein the adhesive is provided on the outer surface of the expandable member prior to the act of inserting the applier and the expandable member through a patient's esophagus.

3. A method of forming a gastric flow restriction with an applier, an expandable member, and an adhesive, the applier comprising an elongate shaft, a distal tip, a vacuum lumen extending longitudinally through the elongate shaft and through the distal tip, and an inflation lumen separate from the vacuum lumen, wherein a first portion of the inflation lumen is positioned parallel to the vacuum lumen, wherein a second portion of the inflation lumen is oriented at an angle in relation to the vacuum lumen, wherein the first portion and the second portion of the inflation lumen are connected at an angled bend, wherein the inflation lumen is further configured to be selectively coupled with the expandable member, the expandable member comprising an outer surface, wherein the expandable member is in fluid communication with the inflation lumen, wherein a portion of the expandable member defines an opening extending through the entire expandable member, the method comprising;
(a) applying the adhesive to the outer surface of the expandable member;
(b) inserting the applier and the expandable member through the esophagus of the patient and into the stomach of the patient, wherein the applier is positioned such that the applier extends through the opening of the expandable member with the distal tip positioned below the expandable member during the act of inserting;
(c) drawing the inner walls of the patient's stomach towards the expandable member with a suction created by the vacuum lumen;
(d) establishing sealed communication between the inflation lumen and the expandable member;
(e) delivering a fluid to the expandable member to inflate the expandable member, wherein the fluid is delivered through the inflation lumen, wherein the distal tip acts as a barrier to prevent the lower portion of the stomach from interfering with the inflation of the expandable member during the act of delivering a fluid;
(f) stopping the delivery of the fluid to the expandable member after at least a portion of the outer surface of the expandable member adheres to the inner wall of the patient's stomach; and
(g) withdrawing the applier through the opening of the expandable member and further through the esophagus of the patient.

4. A method of using an applier and an expandable member to form a gastric restriction, wherein the applier comprises an elongate shaft and a distal tip, wherein the applier is dimensioned to fit in an esophagus, wherein the elongate shaft comprises a vacuum lumen extending longitudinally through the applier, wherein the applier has a conduit configured to communicate a fluid medium, wherein a first portion of the conduit is configured to run parallel to the elongate shaft, wherein a second portion of the conduit is connected to the first portion of the conduit at an angle, wherein the second portion of the conduit is further configured to selectively couple with the expandable member, wherein the applier comprises a pair of deployable arms having an undeployed position and a deployed position, wherein the pair of deployable arms in the undeployed position are positioned parallel to the elongate shaft, wherein the pair of deployable arms in the deployed position are positioned approximately perpendicular to the elongate shaft thereby forming a horizontal platform, wherein the expandable member has an outer surface, a corresponding outer circumference, and a stoma extending therethrough, wherein the expandable member has a toroidal shape, wherein the expandable member is configured to expand from a non-expanded configuration to an expanded configuration, the method comprising:
(a) retaining the pair of deployable arms in the undeployed position;
(b) inserting the applier and the expandable member through a patient's esophagus until the expandable member and at least a portion of the applier reach the patient's stomach, wherein the applier is positioned through the stoma of the expandable member during the act of inserting the applier and the expandable member with the distal tip positioned below the expandable member during the act of inserting;
(c) deploying the pair of deployable arms from the undeployed position to the deployed position by sweeping the pair of deployable arms outwardly toward the esophagus, wherein the act of deploying forms a horizontal platform with the deployable arms;
(d) drawing the inner walls of a patient's stomach towards the expandable member by using a suction communicated through the vacuum lumen;
(e) expanding the expandable member within the patient's stomach while the applier is positioned through the stoma of the expandable member, wherein the act of expanding comprises communicating a fluid medium through the conduit, wherein during the act of expanding, at least a portion of the expandable member is supported by the platform formed by the pair of deployable arms, wherein the distal tip acts as a barrier to prevent the lower portion of the stomach from interfering with the expandable member during the act of expanding the expandable member;
(f) adhering a portion of the outer surface of the expanded expandable member to the inner wall of the patient's stomach with an adhesive such that an area of contact between the inner wall of the patient's stomach and the outer surface of the expandable member defines a band corresponding to the outer circumference of the expandable member to form a gastric flow restriction such that any food traveling from the esophagus to the duodenum passes through the stoma of the expandable member;
(g) retracting the pair of deployable arms, wherein the act of retracting the pair of deployable arms comprises inwardly sweeping the pair of deployable arms such that the pair of deployable arms sweep to position the pair of deployable arms substantially parallel to the elongate shaft; and
(h) withdrawing the applier through the opening of the expandable member and further through the esophagus of the patient.

* * * * *